US009196465B2

(12) United States Patent
Nie et al.

(10) Patent No.: US 9,196,465 B2
(45) Date of Patent: Nov. 24, 2015

(54) METHOD AND KIT FOR DETECTING HEPCIDIN

(75) Inventors: Guangjun Nie, Beijing (CN); Tony Hu, Beijing (CN); Jia Fan, Beijing (CN); Yuliang Zhao, Beijing (CN); Mauro Ferrari, Beijing (CN)

(73) Assignee: National Center for Nanoscience and Technology, Beijing (CN)

( * ) Notice: Subject to any disclaimer, the term of this patent is extended or adjusted under 35 U.S.C. 154(b) by 0 days.

(21) Appl. No.: 14/123,679

(22) PCT Filed: Jun. 1, 2012

(86) PCT No.: PCT/CN2012/076366
§ 371 (c)(1),
(2), (4) Date: Apr. 10, 2014

(87) PCT Pub. No.: WO2012/163286
PCT Pub. Date: Dec. 6, 2012

(65) Prior Publication Data
US 2014/0217277 A1   Aug. 7, 2014

(30) Foreign Application Priority Data

Jun. 3, 2011 (CN) .......................... 2011 1 0149663

(51) Int. Cl.
*A61K 38/00* (2006.01)
*C07K 2/00* (2006.01)
*C07K 4/00* (2006.01)
*C07K 5/00* (2006.01)
*C07K 7/00* (2006.01)
*C07K 14/00* (2006.01)
*C07K 17/00* (2006.01)
*G01N 1/00* (2006.01)
*B01D 59/44* (2006.01)
*H01J 49/00* (2006.01)
*G01N 33/68* (2006.01)
*G01N 33/74* (2006.01)
*G01N 1/38* (2006.01)

(52) U.S. Cl.
CPC ............. *H01J 49/0027* (2013.01); *G01N 1/38* (2013.01); *G01N 33/6848* (2013.01); *G01N 33/74* (2013.01); *H01J 49/00* (2013.01)

(58) Field of Classification Search
CPC ..... G01N 1/38; G01N 33/6848; G01N 33/74; H01J 49/00; H01J 49/0027
See application file for complete search history.

(56) References Cited

U.S. PATENT DOCUMENTS 8,313,950 B2 * 11/2012 Rovin et al. ..................... 436/86

FOREIGN PATENT DOCUMENTS

CN    101358201      2/2009
WO   2007120248    10/2007
WO   2008048508     4/2008

OTHER PUBLICATIONS

Hu et al. The Next Generation of Proteomic Nanochips in Biomarker Discovery. NSTI-Nanotech 2009, vol. 3, 2009, pp. 238-241.*
Qiagen. Mass Spec Turbo Chip Handbook For high-throughput MALDI-MS analysis of peptides and proteins. Apr. 2006, second edition, 40 pages.*
Chau. A review of techniques for measurement of contact angles and their applicability on mineral surfaces. Minerals Engineering, 2009. vol. 22, pp. 213-219.*
Lelah et al. The measurement of contact angles on circular tubing surfaces using the captive bubble technique. J Biomed Mat Res, 1985. vol. 19, pp. 1011-1015.*
Anderson et al., "High-Throughput Matrix-Assisted Laser Desorption Ionization-Time-of-Flight Mass Spectrometry Method for Quantification of Hepcidin in Human Urine," Anal. Chem. (2010) 82:1551-1555.
Anderson et al., "Design and Validation of a High-Throughput Matrix-Assisted Laser Desorption Ionization Time-of-Flight Mass Spectrometry method for Quantification of Hepcidin in Human Plasma," Anal. Chem (2011) 83:8357-8362.
Bansal et al., "Quantification of hepcidin using matrix-assisted laser desorption/ionization time-of-flight mass spectrometry," Rapid Commun. Mass Spectrom (2009) 23:1531-1542.
Gay et al., "Quantitative assay of urinary hepcidin using MALDI-TOF mass spectrometry," Anal. Methods (2010) 2:268-274.
Hassan et al., "Characterization and Quantization of Hepcidin from Human and Mouse Serum and Secretion Medium from Human Liver Cell Line, HU.7 by MALDI-TOF Mass Spectrometry," Journal of Proteins and Proteomics (2012) 3(3):177-185.
Xueao et al., "Preparation of Ordered Mesoporous Silica Thin Films and Their Assembly Chemistry," Progress in Chemistry (2006) 18(10):1322-1329.

* cited by examiner

*Primary Examiner* — Marcela M Cordero Garcia
(74) *Attorney, Agent, or Firm* — Volpe and Koenig, P.C.

(57) ABSTRACT

A method for detecting hepcidin. Having a sample liquid in contact with a nanochip having a specific surface coating structure of silicon oxide, so that hepcidin is enriched with specificity; eluting the nanochip with an eluent; by performing mass spectrometric detection on the elution product, determining the hepcidin content in the elution product. The enrichment method substantially enhances the sensitivity and accuracy of mass spectrometric detection. A kit for detecting hepcidin comprising a sample diluent and a nanochip, the sample diluent comprising water, trifluoroacetic acid, and acetonitrile.

13 Claims, 3 Drawing Sheets

METHOD AND KIT FOR DETECTING HEPCIDIN

This application is a 35 U.S.C. §371 national stage application of PCT/CN2012/076366, which was filed Jun. 1, 2012 and is incorporated herein by reference as if fully set forth.

FIELD OF THE INVENTION

The present invention relates to a method for detecting biomolecular and a kit, in particular to a method for detecting hepcidin and a kit for detecting hepcidin.

BACKGROUND OF THE INVENTION

Hepcidin is a type of antibacterial peptide that has broad-spectrum bactericidal and bacteriostatic effect, and belongs to the defensive protein family. When hepcidin gene is translated in liver, it generates a type of early polypeptide first; then, after the signal peptide of the early polypeptide is removed by enzyme digestion, it forms a pro-hepcidin; and then the pro-hepcidin is transported into blood circulation, and finally is sheared by propeptide convertase to form a mature hepcidin.

Hepcidin is related with hereditary hemochromatosis, anemia, iron metabolism disorders, chronic kidney diseases, and inflammatory reactions, etc.; however, the diagnostic result of the above-mentioned diseases can't be derived from the detection result of hepcidin directly owing to the existence of influencing factors such as individual differences; instead, the diagnostic result needs to be judged comprehensively depending on other influencing factors. Accordingly, qualitative and/or quantitative detection of hepcidin can provide intermediate information for diagnosis of the above-mentioned diseases.

It is very important to develop a simple and quick method for detecting hepcidin qualitatively and/or quantitatively. However, hepcidin that is of clinical detection significance only has 25 amino acids and its immunogenicity is very low; therefore, it is very difficult to obtain the corresponding antibody; whereas, most existing antibody-based detection methods, when used for detection, can't distinguish pro-hepcidin and hepcidin. In addition, the existing mass-spectrometry-based method for detecting hepcidin is usually: treating the sample that is suspected as containing hepcidin (e.g., serum and/or plasma sample) by mass-spectrometric sample pre-treatment (e.g., chromatographic separation or enrichment with a nano chip, etc.), and followed by mass spectrometric detection, and determining whether the sample contains hepcidin or determining the content of hepcidin in the sample according to the mass spectrometric detection result. The existing mass-spectrometry-based method for detecting hepcidin has low sensitivity and poor accuracy, owing to the fact that the quality of the sample to be injected for mass-spectrometric detection is still poor though it has been treated by mass-spectrometric sample pre-treatment such as chromatographic separation or enrichment with a nano chip.

SUMMARY OF THE INVENTION

To overcome the drawback of low sensitivity and poor accuracy of the existing mass-spectrometry-based method for detecting hepcidin in the prior art, the present invention provides a method for detecting hepcidin and a kit for detecting hepcidin.

The inventor of the present invention has found that hepcidin can be enriched specifically with a nano chip that has a specific surface coating structure, so that the sensitivity and accuracy of the mass-spectrometry-based method for detecting hepcidin can be improved. Thus, the present invention is obtained.

The present invention provides a method for detecting hepcidin, comprising the following steps:
(1) controlling a sample liquid to contact with a nano chip, and then removing the sample liquid to obtain a nano chip that has been in contact with sample, wherein, the sample liquid contains or doesn't contain hepcidin;
(2) eluting the nano chip that has been in contact with the sample liquid with an eluent, to obtain an eluate, wherein, the eluent can dissolve hepcidin;
(3) obtaining the mass spectrometric detection result of the eluate obtained in step (2);
(4) determining whether the eluate contains hepcidin or determining the content of hepcidin in the eluate, according to the mass spectrometric detection result;

In step (1), the nano chip comprises a substrate and a porous silicon oxide coating attached to the substrate, wherein, the average pore size of the porous silicon oxide coating is 3.65-3.75 nm, the specific surface area of the porous silicon oxide coating is 1,050-1,200 $m^2/g$, and the porous silicon oxide coating has a plurality of pore canals that are axially parallel to each other, every 7 pore canals among the pore canals form a pore canal group, each of which comprises 1 central pore canal and 6 peripheral pore canals that are adjacent to and surround the central pore canal, and the lines connecting the cross section centers of adjacent peripheral pore canals among the 6 peripheral pore canals form a regular hexagon.

Furthermore, the inventor of the present invention has found that by mixing a sample diluent that contains acetonitrile and trifluoroacetic acid with the sample, the sensitivity and accuracy of the method for detecting hepcidin can be improved further.

Thus, the present invention further provides a kit for detecting hepcidin, comprising:
(i) a sample diluent, which contains trifluoroacetic acid and acetonitrile;
(ii) a nano chip, which comprises a substrate and a porous silicon oxide coating attached to the substrate, wherein, the average pore size of the porous silicon oxide coating is 3.65-3.75 nm, the specific surface area of the porous silicon oxide coating is 1,050-1,200 $m^2/g$, and the porous silicon oxide coating has a plurality of pore canals that are axially parallel to each other, every 7 pore canals among the pore canals form a pore canal group, each of which comprises 1 central pore canal and 6 peripheral pore canals that are adjacent to and surround the central pore canal, and the lines connecting the cross section centers of adjacent peripheral pore canals among the 6 peripheral pore canals form a regular hexagon.

With the method for detecting hepcidin provided in the present invention, the sensitivity and accuracy of the mass-spectrometry-based method for detecting hepcidin is significantly improved; especially, the detection result of hepcidin in complex samples (e.g., serum) is improved; for example, in the case of detecting human hepcidin, take rabbit serum that contains 2.5 nM human hepcidin as a sample, the method for detecting hepcidin provided in the present invention can achieve a SNR (Signal Noise Ratio) greater than 3 and a variation coefficient smaller than 15%, which indicates the method for detecting hepcidin provided in the present invention is superior to the existing mass-spectrometry-based method for detecting hepcidin; for example, by mass spectrometric sample pre-treatment with a nano chip having a porous silicon oxide coating, whose pores have a 3.9 nm average pore size, are in spherical shape, communicate with each other, and are arranged in 3D, the mass-spectrometry-based method for detecting hepcidin will result in a SNR as low as 1.5 and a variation coefficient as high as 25%.

Other characteristics and advantages of the present invention will be further detailed in the specific embodiments hereunder.

DETAILED DESCRIPTION OF THE EMBODIMENTS

Figure 1:
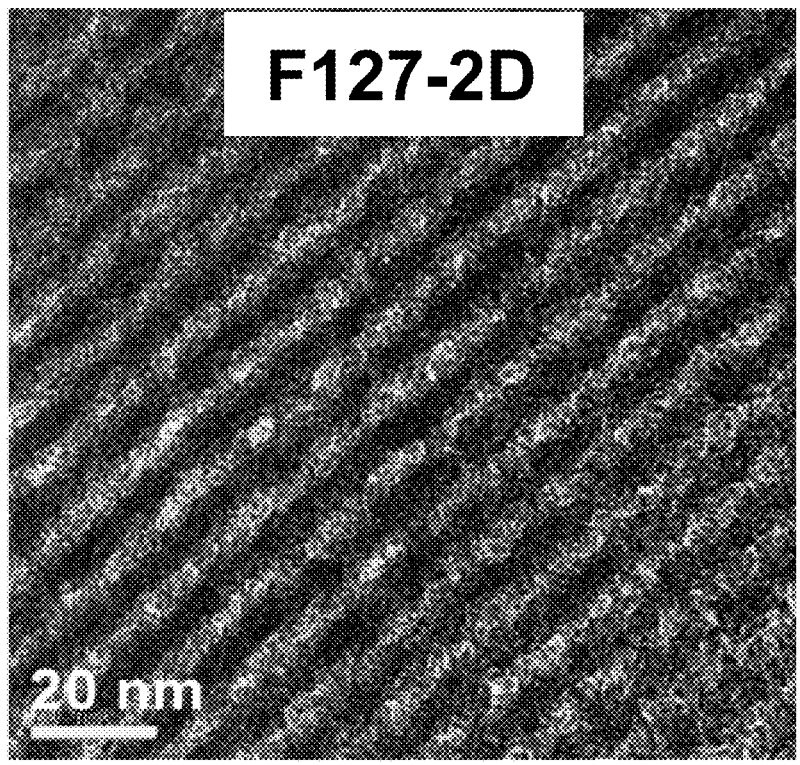
FIG. 1 is a SEM (Scanning Electron Microscope) image of the porous silicon oxide coating on the nano chip in Preparation Example 1.

Hereinafter the embodiments of the present invention will be detailed with reference to the accompanying drawings. It should be understood that the embodiments described here are used to describe and explain the present invention, but not to intend to limit the present invention.

In the present invention, unless otherwise specified, the coverage of the term "solution" is not limited to dispersion systems (true solutions) comprising dispersate with a particle diameter smaller than 1 nm; instead, the term "solution" generally refers to a homogeneous liquid mixture, which can include colloidal dispersion (colloidal solution).

In the present invention, unless otherwise specified, the volumetric values of gas and liquid all refer to values under standard conditions.

The present invention provides a method for detecting hepcidin, comprising the following steps:
(1) controlling a sample liquid to contact with a nano chip, and then removing the sample liquid to obtain a nano chip that has been in contact with sample, wherein, the sample liquid contains or doesn't contain hepcidin;
(2) eluting the nano chip that has been in contact with the sample liquid with an eluent, to obtain an eluate, wherein, the eluent can dissolve hepcidin;
(3) obtaining the mass spectrometric detection result of the eluate obtained in step (2);
(4) determining whether the eluate contains hepcidin or determining the content of hepcidin in the eluate, according to the mass spectrometric detection result;

In step (1), the nano chip comprises a substrate and a porous silicon oxide coating attached to the substrate, wherein, the average pore size of the porous silicon oxide coating is 3.65-3.75 nm, the specific surface area of the porous silicon oxide coating is 1,050-1,200 m$^2$/g, and the porous silicon oxide coating has a plurality of pore canals that are axially parallel to each other, every 7 pore canals among the pore canals form a pore canal group, each of which comprises 1 central pore canal and 6 peripheral pore canals that are adjacent to and surround the central pore canal, and the lines connecting the cross section centers of adjacent peripheral pore canals among the 6 peripheral pore canals form a regular hexagon.

The inventor of the present invention has found that a nano chip with porous silicon oxide coating that has the above-mentioned structure is especially suitable for enriching hepcidin specifically; thus, the sensitivity and accuracy of the mass-spectrometry-based method for detecting hepcidin can be improved.

In the present invention, unless otherwise specified, the term "average pore size" refers to the value obtained by measurement with an $N_2$ adsorption/desorption method and by calculation. For example, obtaining the $N_2$ adsorption/desorption isotherm at 77K with an adsorption instrument (e.g., Quantachrome), and then the average pore size can be obtained by calculation with Barrett-Joyner-Halenda (BJH) method according to the desorption isotherm branch.

In the present invention, unless otherwise specified, the term "specific surface area" refers to the value obtained by measurement with an $N_2$ adsorption/desorption method and by calculation. For example, obtaining the $N_2$ adsorption/desorption isotherm at 77K with an adsorption instrument (e.g., Quantachrome), and then the specific surface area can be obtained by calculation with Brunauer-Emmett-Teller (BET) method according to the $N_2$ adsorption/desorption isotherm.

In the present invention, the porous silicon oxide coating has a plurality of pore canals that are axially parallel to each other, and every 7 pore canals among the pore canals form a pore canal group; thus, a plurality of pore canal groups are formed in the porous silicon oxide coating, and each of the pore canal groups comprises 1 central pore canal and 6 peripheral pore canals that are adjacent to and surround the central pore, and the structure that the lines connecting the cross section centers of adjacent peripheral pore canals among the 6 peripheral pore canals form a regular hexagon refers to the structure of the nano chip observed in TEM (Transmission electron microscope) images, for example, the structure shown in FIG. 1.

In the present invention, it should be noted: in the inner side of the porous silicon oxide coating, the pore canal group can be formed by all 7 pore canals; at the edges of the porous silicon oxide coating, the pore canal group can be formed by 2-6 pore canals.

In addition, in the TEM images of the nano chip, it can be seen that the pore canals are axially parallel to the tangent plane of the substrate surface.

The substrate can be any conventional substrate in the bio-chip field, such as silicon wafer, glass sheet, metal sheet, or ceramic sheet. There is no special requirement for the size and thickness of the substrate, which is to say, the substrate can has an ordinary size and thickness in the biochip field, for example, the substrate can be a wafer having a diameter of 3-15 cm, and the thickness of the substrate can be 100-1,000 µm.

A nano chip that meets the above requirements in step (1) can be prepared with the following method:
(a) homogeneously mixing silicic acid solution with ethanol solution containing surfactant to obtain a coating material;

The silicic acid solution can be obtained from a mixture after being mixed homogeneously, the mixture can contain tetraethyl orthosilicate, ethanol, water, and hydrochloric acid; and in the mixture, relative to 1 g tetraethyl orthosilicate, the dosage of ethanol can be 1-1.15 ml, the dosage of water can be 0.4-0.6 ml, and the dosage of hydrochloric acid can be 0.15-0.25 mmol (calculated by HCl). The conditions for preparing the silicic acid solution by mixing can include: 60-90° C. mixing temperature and 1-3 h mixing duration.

In the ethanol solution containing surfactant, relative to 1 g surfactant, the content of ethanol can be 3.5-4.5 ml.

The surfactant can be a polymer having an general formula $PEO_m$-$PPO_n$-$PEO_m$, and m can be an integer within 100-110 range and n can be an integer within 65-75 range. Wherein, PEO represents polyethylene oxide unit, and PPO represents polypropylene oxide unit. The polymers that meet the above requirements can be commercially available. For example, the product with Pluronic F127 from BASF can be used as the surfactant.

Relative to 1 ml silicic acid solution, the dosage of the ethanol solution containing surfactant can be 0.8-1.2 ml. The conditions for preparing the coating material by mixing can include: 10-35° C. mixing temperature and 1-3 h mixing duration.

(b) applying the coating material obtained in step (a) on the substrate, and then curing the coating.

In step (b), the coating material can be applied by spin-coating. The conditions for spin-coating can include: 500-3,500 rpm spinning speed, and 0.01-0.05 ml dosage of coating material relative to per 1 $cm^2$ coating area. A conventional spin-coating device can be used to attain the above-mentioned spin-coating conditions. In step (b), the curing conditions can include: 300-550° C. curing temperature and 3-8 h curing duration. In step (b), the curing temperature can be reached by a gradient heating way at a 0.5-5° C./min heating rate. In step (b), the substrate coated with the coating material can be kept at 70-90° C. for 8-16 h before curing. In step (b), the cured product can be cooled down by natural cooling for 8-20 h after curing.

In the preparation method described above, the surfactant, the dose ratio of surfactant to tetraethyl orthosilicate, the concentration of the surfactant and tetraethyl orthosilicate in the coating material, and the spin-coating conditions are specifically determined to ensure the nano chip prepared with the method described above has the following features: the average pore size of the porous silicon oxide coating is 3.65-3.75 nm, the specific surface area of the porous silicon oxide coating is 1,050-1,200 $m^2/g$, and the porous silicon oxide coating has a plurality of pore canals that are axially parallel to each other, every 7 pore canals among the pore canals form a pore canal group, each of which comprises 1 central pore canal and 6 peripheral pore canals that are adjacent to and surround the central pore canal, and the lines connecting the cross section centers of adjacent peripheral pore canals among the peripheral pore canals form a regular hexagon; in addition, the nano chip prepared with the method described above can be exactly right used in the technical solutions of the present invention and can solve the technical problems of the present invention.

The inventor of the present invention has found that the nano chips that have better water wettability can specifically enrich hepcidin more effectively, and thereby the sensitivity and accuracy of the method for detecting hepcidin can be further improved. Thus, a preferred embodiment of the present invention is provided.

According to a preferred embodiment of the present invention, the contact angle of the surface of the porous silicon oxide coating is smaller than 15°.

In the present invention, unless otherwise specified, the term "contact angle" refers to an included angle from the solid-liquid interface, through the inner side of the liquid, to the vapor-liquid interface at the boundaries of solid phase, liquid phase and vapor phase. The smaller the contact angle is, the better the wettability will be. In the present invention, the value of the term "contact angle" used is the value obtained by observing the contour of liquid drop or gas bubble on solid surface, drawing tangent lines at the point of intersection among solid phase, liquid phase and vapor phase, and measuring the angle directly with a protractor according to the method described in literature (Lelah, Michael D, the Measurement of Contact Angles on Circular Tubing Surfaces Using the Captive Bubble Technique; J. Biomed. Mater. Res.; 19(9); 1011-1015; 1985). In addition, the liquid used here is water.

To ensure the contact angle of the surface of the porous silicon oxide coating is smaller than 15°, the cured product after being cooled down can be treated with oxygen plasma.

The conditions for the treatment with oxygen plasma can include: 70-90 standard ml/min (sccm) oxygen flow rate, 250-350 W power, and 5-15 min duration relative to 70 $cm^2$ outside surface area of the porous silicon oxide coating. The conditions for the treatment with oxygen plasma can be attained with a plasma asher.

According to the method provided in the present invention, in step (1), the contact conditions can include: contact temperature, 10-37° C., preferably 15-30° C.; contact duration, 20-60 min, preferably 30-50 min.

Furthermore, the inventor of the present invention has further found that by mixing a sample diluent that contains acetonitrile and trifluoroacetic acid with the sample, the sensitivity and accuracy of the method for detecting hepcidin can be improved further; thus, another preferred embodiment of the present invention is provided.

According to another preferred embodiment of the present invention, the sample liquid contains sample and a sample diluent; and the sample diluent contains water, trifluoroacetic acid, and acetonitrile.

Wherein, the sample can be any excised biomaterial, such as excised body fluid and tissues; preferably, the sample is one or more of serum, plasma, urine, and cerebrospinal fluid.

Wherein, relative to 1 volume of the sample liquid, the dosage of the sample diluent may allows the dosage of trifluoroacetic acid to be 0.00005-0.00015 volume and the dosage of acetonitrile to be 0.03-0.07 volume.

Wherein, in the sample diluent, relative to 1 volume of water, the content of trifluoroacetic acid can be 0.001-0.003 volume, and the content of acetonitrile can be 0.5-1.5 volume.

According to the method described in the present invention, relative to per square millimeter outside surface area of the porous silicon oxide coating, the dosage of the sample liquid can be 0.5-4 μl.

To enrich different samples on the same nano chip, a separating material can be attached to the porous silicon oxide coating on the nano chip, to separate the nano chip into a plurality of separate zones. Each zone and the separating material that separates the zone form a pool. The operations described in step (1)-(3) can be executed independently in different pools.

There is no special requirement for the method for attaching the separating material, as long as the hepcidin can be detected conveniently at high throughput; for example, a silica membrane with a plurality of through-holes can be bonded to the porous silicon oxide coating on the nano chip to form a plurality of separate pools; the through-hole size and thickness of the silica membrane can allows the obtained pools accommodate the sample liquids completely.

Preferably, the silica membrane can be used to form a pools having a 1.5-4.5 mm diameter and a 0.5-1.5 mm depth on the porous silicon oxide coating on the nano chip, and 5-20 μL sample liquid is loaded into each of the pools. As known by those skilled in the art, the volume of sample liquid loaded into each pool should be less than the capacity of the pool, to avoid overflow of the sample liquid.

According to the method provided in the present invention, in step (1), there is no special requirement for the method for removing the sample liquid, as long as the sample liquid attached to the surface of the nano chip can be removed after the contact process. For example, the sample liquid can be removed by sucking after the contact process. To remove the residual sample liquid completely from the porous silicon oxide coating after the contact process, the porous silicon oxide coating can be washed with water for 2-5 cycles, and water in the same volume as the sample liquid can be used in each washing cycle.

According to the method provided in the present invention, to further improve the SNR of mass spectrometric detection, preferably, the step (1) can be repeated for several times; for example, the step (1) can be repeated for 2-5 times. In the present invention, to improve the accuracy of the detection, preferably, the water used is deionized water, for example, the water with conductivity greater than or equal to 18.2 MΩ/cm at 20° C. can be used.

According to the method provided in the present invention, there is no special requirement for the eluent, as long as the eluent can dissolve hepcidin; for example, the eluent can contain trifluoroacetic acid, acetonitrile, and water.

Wherein, in the eluent, relative to 1 volume of water, the content of trifluoroacetic acid can be 0.001-0.003 volume, and the content of acetonitrile can be 0.5-1.5 volume.

Wherein, relative to per square millimeter outside surface area of the porous silicon oxide coating, the dosage of the eluent is 0.3-2 μl.

Wherein, there is no special requirement for the eluting method; for example, the eluent can be controlled to fully wet the part of porous silicon oxide coating after the part contacts with the sample, and then the eluent can be collected to obtain an eluate.

Preferably, when the silica membrane is used to form pools having a 1.5-4.5 mm diameter and a 0.5-1.5 mm depth on the porous silicon oxide coating on the nano chip, and 5-20 μL sample liquid is loaded into each pool, the volume of eluent added to elute each pool can be 3-7 μl.

Compared to the existing method for detecting hepcidin that involves a chromatography-based mass spectrometric sample pre-treatment procedure, the method for detecting hepcidin provided in the present invention is simpler and easier to use.

According to the method provided in the present invention, the method for obtaining the mass spectrometric detection result of the eluate can be any conventional method that utilizes bio-mass spectrometry to detect peptide fragments, and which is well known by those skilled in the art; for example, the method disclosed in "Protein Chemistry and Proteomics" (published by Science Press in 2004) can be used.

Furthermore, the inventor of the present invention has also found that by mixing the sample diluent that contains acetonitrile and trifluoroacetic acid with the sample, the sensitivity and accuracy of the mass-spectrometry-based method for detecting hepcidin can be improved further.

Thus, the present invention further provides a kit for detecting hepcidin, comprising:
  (i) a sample diluent, which contains water, trifluoroacetic acid and acetonitrile;
  (ii) a nano chip, which comprises a substrate and a porous silicon oxide coating attached to the substrate, wherein, the average pore size of the porous silicon oxide coating is 3.65-3.75 nm, the specific surface area of the porous silicon oxide coating is 1,050-1,200 m$^2$/g, and the pore canals in the porous silicon oxide coating are axially parallel to each other, and each pore canal is adjacent to 6 pore canals.

According to the kit provided in the present invention, in the sample diluent, relative to 1 volume of water, the content of trifluoroacetic acid can be 0.001-0.003 volume, and the content of acetonitrile can be 0.5-1.5 volume.

According to the kit provided in the present invention, the nano chip is the same as the nano chip that is used in the method for detecting hepcidin provided in the present invention.

Hereunder the present invention will be further detailed with embodiments. However, the scope of the present invention is not limited to these embodiments. Those skilled in the art can foresee the scope of the present invention reasonably according to the embodiments.

PREPARATION EXAMPLE 1

This preparation example is used to explain the method for preparing the nano chip used in the present invention.

Mix 14 g tetraethyl orthosilicate (TEOS) (from Sigma-Aldrich) with 15 ml ethanol, 6.5 ml deionized water, and 0.5 ml 6 mol/l hydrochloric acid, stir the mixture for 2 h at a 100 rpm stirring speed at 75° C., to form a transparent liquid mixture, i.e., the silicic acid solution.

Add 2.4 g surfactant (from BASF, trade No.: Pluronic F127, structural formula: $PEO_{106}$-$PPO_{70}$-$PEO_{106}$) into 10 ml ethanol, stir the solution at room temperature to dissolve the surfactant, to obtain ethanol solution containing surfactant.

Mix 11 ml ethanol solution containing surfactant with 10 ml silicate collosol, stir the mixed solution for 2 h at 100 rpm stirring speed at room temperature, to obtain a coating material.

Load 1.5 ml coating material onto a silicon wafer that is in 10 cm diameter and 525 μm thickness (from Silicon Quest International, USA), apply the coating material by spin-coating for 40 s at 1500 rpm spinning speed under spin-coating conditions, keep the coating for 12 h at 80° C., and then heat up to 425° C. at a 1° C./min temperature rise rate; keep for 5 h at 425° C., and then cool down the coating by natural cooling for 12 h, to obtain a coated nano chip.

Measure $N_2$ adsorption/desorption isotherm with a Quantachrome adsorption instrument at 77K condition, and calculate with Barrett-Joyner-Halenda (BJH) method according to the desorption isotherm branch to obtain the average pore size of the porous silicon oxide coating on the nano chip obtained in this preparation example, the average pore size is 3.7 nm; calculate with Brunauer-Emmett-Teller (BET) method according to the $N_2$ adsorption/desorption isotherm to obtain the specific surface area of the porous silicon oxide coating on the nano chip obtained in this preparation example, the specific surface area is 1131 m$^2$/g. Use a TEM to observe the structure of the porous silicon oxide coating on the nano chip obtained in this preparation example at the condition of 200 kV acceleration voltage. The result is shown in FIG. 1. It can be seen: the porous silicon oxide coating has a plurality of pore canals that are axially parallel to each other, and every 7 pore canals among the pore canals form a pore canal group, each of which comprises 1 central pore canal and 6 peripheral pore canals that are adjacent to and surround the central pore canal, and the lines connecting the cross section centers of adjacent peripheral pore canals among the 6 peripheral pore canals form a regular hexagon. In addition, in the TEM images of the nano chip, it can be seen that the axes of the pore canals are parallel to the substrate surface or the tangent plane of the substrate surface.

With the method described in literature (Lelah, Michael D, the Measurement of Contact Angles on Circular Tubing Surfaces Using the Captive Bubble Technique; J. Biomed. Mater.

Res.; 19(9); 1011-1015; 1985), observe the contour of liquid drop or gas bubble on solid surface, draw tangent lines at the point of intersection among solid phase, liquid phase and vapor phase, and measure the angle directly with a protractor to obtain the contact angle of the porous silicon oxide coating on the nano chip obtained in this preparation, example the contact angle is greater than 30°; in addition, the liquid used here is water.

PREPARATION EXAMPLE 2

This preparation example is used to describe the method for preparing a nano chip with porous silicon oxide coating that has a contact angle smaller than 15° used in the present invention.

In this preparation example, the nano chip is prepared with the same method as used in Preparation Example 1, except for the following difference: treat the cured product by plasma oxygen treatment with a plasma asher for 10 min under the conditions of 80 standard ml/min (sccm) oxygen flow rate and 300 W power, to obtain the nano chip in this preparation example.

With the same method as used in Preparation Example 1, the average pore size and the specific surface area of the porous silicon oxide coating on the nano chip obtained in this preparation example are measured to be 3.7 nm and 1125 $m^2$/g respectively; the pore canals in the porous silicon oxide coating exhibit a structure that the pore canals are axially parallel to each other and each pore canal is adjacent to 6 pore canals, and the contact angle of the porous silicon oxide coating is smaller than 15°.

PREPARATION EXAMPLE 3

This preparation example is used to describe the method for preparing the nano chip that is not suitable for the present invention.

In this preparation example, the nano chip is prepared with the same method as used in Preparation Example 1, except for the following difference: add 1.5 g surfactant (from BASF, trade No.: Pluronic F127, structural formula: $PEO_{106}$-$PPO_{70}$-$PEO_{106}$) into 10 ml ethanol, stir the solution at room temperature to dissolve the surfactant, to obtain the ethanol solution containing surfactant.

Figure 2:
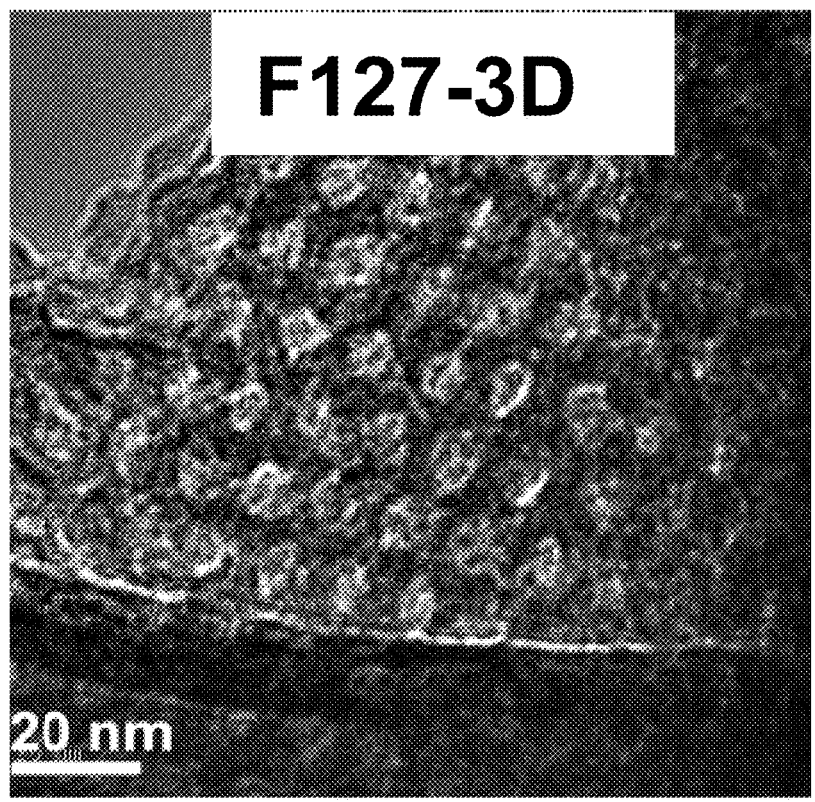
FIG. 2 is a SEM image of the porous silicon oxide coating on the nano chip in Preparation Example 3.

With the same method as used in Preparation Example 1, the average pore size and the specific surface area of the porous silicon oxide coating on the nano chip obtained in this preparation example are measured to be 3.9 nm and 640 $m^2$/g respectively; the TEM image is shown in FIG. 2; it can be seen: the pores are in spherical shape, there is no pore canal structure, the pores communicate with each other, the arrangement of the pores is in 3D, and the contact angle of the porous silicon oxide coating is greater than 30°.

PREPARATION EXAMPLE 4

This preparation example is used to describe the method for preparing the nano chip that is not suitable for the present invention.

In this preparation example, the nano chip is prepared with the same method as used in Preparation Example 1, except for the following difference: add 1.2 g surfactant (from BASF, trade No. Pluronic L121, structural formula: $PEO_5$-$PPO_{70}$-$PEO_5$) into 10 ml ethanol, stir the solution at room temperature to dissolve the surfactant, to obtain the ethanol solution containing surfactant.

With the same method as used in Preparation Example 1, the average pore size and the specific surface area of the porous silicon oxide coating on the nano chip obtained in this preparation example are measured to be are 6 nm and 587 $m^2$/g respectively; the TEM image indicated that the pores are in an irregular layout, and the contact angle of the porous silicon oxide coating is greater than 30°.

EXAMPLE 1

This example is used to explain the method and the kit for detecting hepcidin provided in the present invention.

It is known that the molecular weight difference between rabbit hepcidin and human hepcidin is apparent, and the MALDI-TOF mass spectrometric analysis result indicates that the rabbit serum has no interference at 2788 Da and 2465 Da. Therefore, rabbit serum (from GIBICO) is used as the diluting serum. Synthetic human hepcidin is used as standard sample (from Sigma-Aldrich, average molecular weight: 2789.4 Da). Adrenocorticotrophic hormone segment 18-39 (ACTH18-39, from Sigma-Aldrich, monoisotopic molecular weight: 2464.2 Da) is used as a reference compound for quantitation of the hepcidin.

Mix 50 ml acetonitrile (chromatographically pure, from Sigma-Aldrich) and 0.1 ml trifluoroacetic acid (chromatographically pure, from Sigma-Aldrich), and add water till the total volume is 100 ml, to obtain the sample diluent to be used in this example. the combination of the sample diluent obtained in this example and the nano chip obtained in Preparation Example 2 is used as a kit in this example. Mix 50 ml acetonitrile (chromatographically pure, from Sigma-Aldrich) and 0.1 ml trifluoroacetic acid (chromatographically pure, from Sigma-Aldrich), and add water till the total volume is 100 ml, to obtain an eluent.

Dissolve 25 pmol standard sample in 10 ml rabbit serum, to obtain 2.5 nmol/l standard rabbit serum sample. Mix 900 μl standard rabbit serum sample and 100 μl sample diluent homogeneously, to obtain a sample liquid.

Cut pores in 3.5 mm diameter on a piece of transparent silica membrane (thickness: 1.2 mm, hardness: 40, with a 3M bonding layer on one side, from McMaster-Carr) and bond the silica membrane onto the porous silicon oxide coating on the nano chip obtained in Preparation Example 2 to form pools in 3.5 mm diameter and 1.2 mm depth, take 10 μl sample liquid and add it in droplets into a pool; to avoid volatilization of the sample liquid, keep the sample liquid under wet box incubation conditions for 40 min, and then suck away the liquid in the pool, and wash the pool with deionized water for 3 cycles (use 10∥l deionized water of each cycle). Next, add 5 μL eluent into each pool, till the pool is wetted fully, and then collect the eluent after wetting, to obtain eluted sample. Measure the eluted sample by matrix assisted laser desorption ionization—time of flight mass spectrometry (MALDI-TOF-MS) (using the reference compound described above) according to the method described in "Protein Chemistry and Proteomics" (published by Science Press in 2004), to obtain the mass spectrometric detection result.

Specifically, the method for obtaining the mass spectrometric detection result is: take 1 μl eluted sample or blank eluent and add it in droplets into the acquisition zone of a MSP96 mass spectrometric target, wait till the sample being dried naturally, and then add 1 μl 4 g/l α-cyanogen-4-hydroxy-cinnamic acid (HCCA, from Burker Daltonics, Germany) in droplets, and wait till the sample being dried naturally. When detecting, the MALDI-TOF-MS (Miroflex, from Bruker Daltonics) with reflection mode is to be calibrated with polypeptide calibration standard (from Bruker Daltonics, Germany) first, which allows the monoisotopic peak deviation smaller than 10 ppm; next, collect data under the condition of 40% relative laser energy intensity by acquiring 10 points of each sample crystal and acquiring 100 times for each point; the laser pulse frequency is 75 Hz, and the acquisition range of mass-to-charge ratio is 1,000-4,000 m/z. After detecting, process the acquired data with FlexAnalysis software, and process the mass spectrogram in the data with a snap method, calculate the peak area of hepcidin obtained from each sample (monoisotopic peak located in a set of mass spectrometric peaks at 2,788.1 m/z, as shown in FIG. 3), and the obtained average peak area of the 10 points collected for each eluted sample or blank eluent is used as the signal value of the eluted sample or blank eluent.

Figure 3:
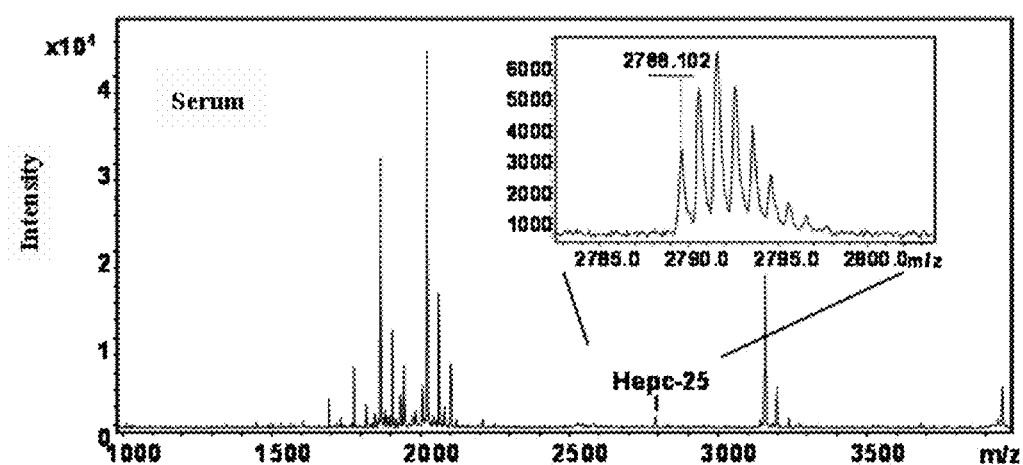
FIG. 3 shows the characteristic peak of hepcidin in a mass spectrometric detection result.

In the mass spectrometric detection result, take the signal value of blank eluent at the characteristic peaks of human hepcidin (monoisotopic peak located in a set of mass spectrometric peaks at 2,788.1 m/z, as shown in FIG. 3) as the noise value, and divide the signal value of the eluted sample by the noise value to obtain SNR. Divide the standard deviation of signal values obtained by measuring the eluted sample for 6 times by the average value of the signal values to obtain variation coefficient (CV %).

In this example, the SNR is 10, and the variation coefficient is 5%. According to the reference compound, the measured value of hepcidin concentration is quantified to be 2.44 nmol/l.

EXAMPLE 2

This example is used to explain the method and the kit for detecting hepcidin provided in the present invention.

In this example, the detection for human hepcidin is carried out with the same method as used in example 1, except for the following difference: the sample diluent used is deionized water.

In this example, the SNR is 7, and the variation coefficient is 10%. According to the reference compound, the measured value of hepcidin concentration is quantified to be 2.41 nmol/l.

EXAMPLE 3

This example is used to explain the method and the kit for detecting hepcidin provided in the present invention.

In this example, the detecting for human hepcidin is carried out with the same method as used in example 1, except for the following difference: the nano chip used in this example is the nano chip prepared in Preparation Example 1.

In this example, the SNR is 5, and the variation coefficient is 12%. According to the reference compound, the measured value of hepcidin concentration is quantified to be 2.38 nmol/l.

COMPARATIVE EXAMPLE 1

In this comparative example, the detection for human hepcidin is carried out with the same method as used in example 3, except for the following difference: the nano chip used in this comparative example is the nano chip prepared in Preparation Example 3.

In this comparative example, the SNR is 1.5, and the variation coefficient is 25%. According to the reference compound, the measured value of hepcidin concentration is quantified to be 2.02 nmol/l.

COMPARATIVE EXAMPLE 2

In this comparative example, the detection for human hepcidin is carried out with the same method as used in example 3, except for the following difference: the nano chip used in this comparative example is the nano chip prepared in Preparation Example 4.

In this comparative example, the SNR is 1.2, and the variation coefficient is 35%. According to the reference compound, the measured value of hepcidin concentration is quantified to be 2.12 nmol/l.

It can be seen from the comparison between the example 2 and the example 1: when the sample diluent containing trifluoroacetic acid and acetonitrile is preferably used, the sensitivity and accuracy can be further improved. It can be seen from the comparison between the example 3 and the example 1: when the nano chip with contact angle of the surface of porous silicon oxide coating smaller than 15° is preferably used, sensitivity and accuracy also can be further improved.

EXAMPLE 4

Figure 4:
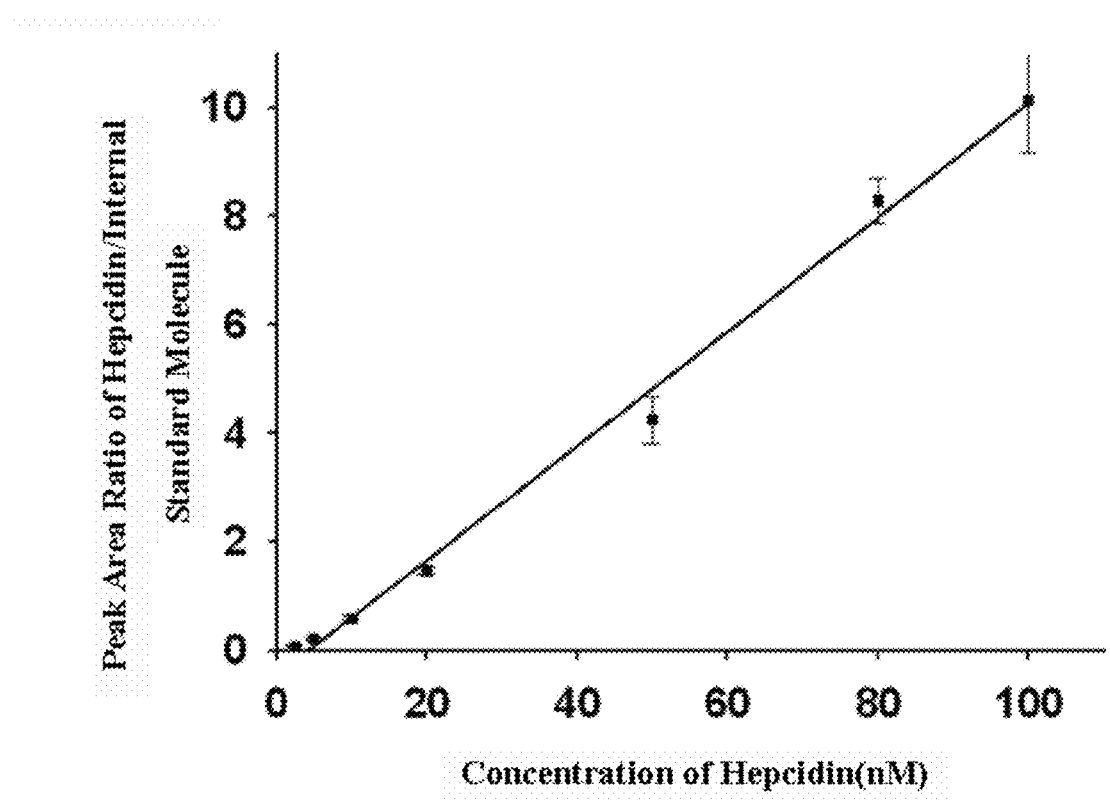
FIG. 4 shows a standard curve of quantitative detection of hepcidin.

Dissolve 10 pmol, 50 pmol, 100 pmol, 200 pmol, 500 pmol, 800 pmol, and 1,000 pmol standard sample that is identical to the standard sample used in example 1 into 10 ml rabbit serum that is identical to the rabbit serum used in example 1 respectively, to obtain 1 nmol/l, 5 nmol/l, 10 nmol/l, 20 nmol/l, 50 nmol/l, 80 nmol/l, and 100 nmol/l standard rabbit serum samples respectively. Detecting these standard rabbit serum samples with the same method as used in example 1 respectively. On the basis of the detection result in example 1 and the detection result in example 4, quantify the concentration of hepcidin according to the reference compound (internal standard molecules), to obtain a standard curve, as shown in FIG. 4. The correlation determination coefficient ($R^2$) of the standard curve is 0.9982, indicating highly creditable linear correlation.

The invention claimed is:
1. A method for detecting hepcidin, comprising the following steps:
   controlling a sample liquid to contact with a nano chip, and then removing the sample liquid to obtain a nano chip that has been in contact with the sample, wherein, the sample liquid contains or doesn't contain hepcidin;
   eluting the nano chip that has been in contact with the sample liquid with an eluent, to obtain an eluate, wherein, the eluent can dissolve hepcidin;
   obtaining a mass spectrometric detection result of the eluate;
   determining whether the eluate contains hepcidin or determining the content of hepcidin in the eluate, according to the mass spectrometric detection result;
   wherein the nano chip comprises a substrate and a porous silicon oxide coating attached to the substrate,
   wherein the average pore size refers to the value obtained by measurement with an $N_2$ adsorption/desorption method and by calculation, the specific surface area refers to the value obtained by measurement with an $N_2$ adsorption/desorption method and by calculation;
   wherein the contact angle of the surface of the porous silicon oxide coating is smaller than 15°, wherein the contact angle used is the value obtained by observing the contour of a water drop on solid surface, drawing tangent lines at the point of intersection among solid phase, liquid phase and vapor phase, and measuring the angle directly with a protractor;

wherein the sample liquid contains sample and a sample diluent; and the sample diluent contains water, trifluoroacetic acid, and acetonitrile.

2. The method according to claim 1, wherein, the contact between the sample liquid and the nanochip conditions include: 10-37° C. contact temperature and 20-60 min contact duration.

3. The method according to claim 1, wherein the sample is one or more of serum, plasma, urine, and cerebrospinal fluid.

4. The method according to claim 3, wherein relative to 1 volume of the sample liquid, the dosage of the sample diluent allows the dosage of trifluoroacetic acid to be 0.00005-0.00015 volume and the dosage of acetonitrile to be 0.03-0.07 volume;
in the sample diluent, relative to 1 volume of water, the content of trifluoroacetic acid is 0.001-0.003 volume, and the content of acetonitrile is 0.5-1.5 volume.

5. The method according to claim 4, wherein relative to per square millimeter outside surface area of the porous silicon oxide coating, the dosage of the sample liquid is 0.5-4 µl.

6. The method according to claim 1, wherein the eluent contains trifluoroacetic acid, acetonitrile, and water; in the eluent, relative to 1 volume of water, the content of trifluoroacetic acid is 0.001-0.003 volume, and the content of acetonitrile is 0.5-1.5 volume; relative to per square millimeter outside surface area of the porous silicon oxide coating, the dosage of the eluent is 0.3-2 µl.

7. A kit for detecting hepcidin, comprising:
a sample diluent, which contains trifluoroacetic acid and acetonitrile;
a nano chip, which comprises a substrate and a porous silicon oxide coating attached to the substrate, wherein the average pore size of the porous silicon oxide coating is 3.65-3.75 nm, the specific surface area of the porous silicon oxide coating is 1,050-1,200 m$^2$/g, and the porous silicon oxide coating has a plurality of pore canals that are axially parallel to each other, every 7 pore canals among the pore canals form a pore canal group, each of which comprises 1 central pore canal and 6 peripheral pore canals that are adjacent to and surround the central pore canal, and the lines connecting the cross section centers of adjacent peripheral pore canals among the 6 peripheral pore canals form a regular hexagon
wherein the average pore size refers to the value obtained by measurement with an $N_2$ adsorption/desorption method and by calculation, the specific surface area refers to the value obtained by measurement with an $N_2$ adsorption/desorption method and by calculation;
wherein the contact angle of the surface of the porous silicon oxide coating is smaller than 15°, wherein the contact angle used is the value obtained by observing the contour of a water drop on solid surface, drawing tangent lines at the point of intersection among solid phase, liquid phase and vapor phase, and measuring the angle directly with a protractor.

8. The kit according to claim 7, wherein in the sample diluent, relative to 1 volume of water, the content of trifluoroacetic acid is 0.001-0.003 volume, and the content of acetonitrile is 0.5-1.5 volume.

9. The method according to claim 2, wherein the sample is one or more of serum, plasma, urine, and cerebrospinal fluid.

10. The method according to claim 1, wherein relative to per square millimeter outside surface area of the porous silicon oxide coating, the dosage of the sample liquid is 0.5-4 µl.

11. The method according to claim 2, wherein relative to per square millimeter outside surface area of the porous silicon oxide coating, the dosage of the sample liquid is 0.5-4 µl.

12. The method according to claim 2, wherein the eluent contains trifluoroacetic acid, acetonitrile, and water; in the eluent, relative to 1 volume of water, the content of trifluoroacetic acid is 0.001-0.003 volume, and the content of acetonitrile is 0.5-1.5 volume; relative to per square millimeter outside surface area of the porous silicon oxide coating, the dosage of the eluent is 0.3-2 µl.

13. The method according to a claim 4, wherein the eluent contains trifluoroacetic acid, acetonitrile, and water; in the eluent, relative to 1 volume of water, the content of trifluoroacetic acid is 0.001-0.003 volume, and the content of acetonitrile is 0.5-1.5 volume; relative to per square millimeter outside surface area of the porous silicon oxide coating, the dosage of the eluent is 0.3-2 µl.

* * * * *